(12) United States Patent
Kojima et al.

(10) Patent No.: US 6,380,179 B1
(45) Date of Patent: Apr. 30, 2002

(54) METHOD FOR TREATMENT OF ALOPECIA

(75) Inventors: Koichi Kojima, Yokohama; Takakazu Hamada, Tokyo; Shiroh Yoshioka, deceased, late of Yokohama, by Hiromi Doi, legal representative; by Hideyuki Yoshioka, legal representative; by Mitsuko Yoshioka, legal representative, both of Nagasaki, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/493,488

(22) Filed: Jan. 28, 2000

Related U.S. Application Data

(63) Continuation-in-part of application No. PCT/JP98/03337, filed on Jul. 27, 1998.

(30) Foreign Application Priority Data

Jul. 29, 1997 (JP) .............................. 9-203136

(51) Int. Cl.⁷ ........................ A61K 31/585; A61P 17/14
(52) U.S. Cl. ........................ 514/176; 514/880
(58) Field of Search ................ 514/176, 880, 514/284

(56) References Cited

U.S. PATENT DOCUMENTS

| | | | |
|---|---|---|---|
| 5,302,621 A | 4/1994 | Kojima et al. | 514/284 |
| 5,567,708 A | 10/1996 | Rasmusson et al. | 514/284 |
| 5,571,817 A | 11/1996 | Rasmusson et al. | 514/284 |
| 5,629,007 A | 5/1997 | Audia et al. | 424/423 |
| 5,635,197 A | 6/1997 | Audia et al. | 424/423 |
| 6,093,722 A | 7/2000 | Kojima et al. | |
| 6,251,915 B1 | 6/2001 | Kojima et al. | |

FOREIGN PATENT DOCUMENTS

| | | |
|---|---|---|
| HU | 218667 | 5/1992 |
| HU | P0001441 | 10/2000 |
| JP | 5-32693 | 2/1993 |
| JP | 5-213987 | 8/1993 |
| JP | 8-73492 | 3/1996 |
| WO | WO 94/17663 | 8/1994 |
| WO | WO 95/10284 | 4/1995 |
| WO | WO 97/117024 | 4/1997 |

OTHER PUBLICATIONS

Linda Rhodes et al., The Effects of Finasteride (Proscar) on Hair Growth, Hair Cycle Stage, and Serum Testosterone and Dihydrotestosterone in Adult Male and Female Stumptail Macaques (*Macaca arctoides*), *Journal of Clinical Endocrinology and Metabolism*, 79, 991–996, (1994).

Jules I. Schwartz et al., "Effect of MK–386, a Novel Inhibitor of Type 1 5α–Reductase, Alone and in Combinations with Finasteride, on Serum Dihydrotestosterone Concentration in Men", *Journal of Clinical Endocrinology and Metabolism*, 81 (1996).

Linda Rhodes et al., "Effects of 1 Year Treatment with Oral MK386, An Inhibitor of Type 1 5α–Reductase, in the Stumptailed Macaque (Macaca Arctoides)", *The Journal of Investigative Dermatology*, 104, 658 (1995).

*Primary Examiner*—Edward J. Webman
*Assistant Examiner*—Helen Nguyen
(74) *Attorney, Agent, or Firm*—Frishauf, Holtz, Goodman, Langer & Chick, P.C.

(57) ABSTRACT

A method of using a specified active ingredient for treating alopecia, female hirsutism and seborrhea and for preventing bone metastasis caused by prostatic cancer. The specified active ingredient is a compound (I) or a pharmaceutically acceptable (i) salt, (ii) ester or (iii) hydrate thereof.

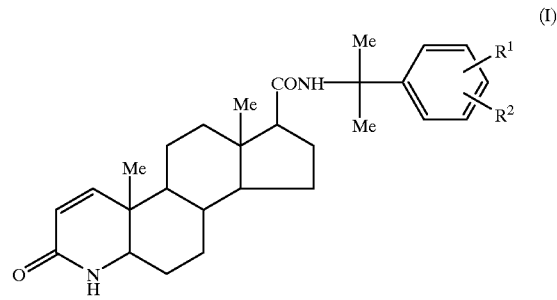

$R^1$, $R^2$: hydrogen atom, hydroxyl group, a protected hydroxyl group or a lower alkoxy group.

6 Claims, No Drawings

```
                        SEQUENCE LISTING

<160> NUMBER OF SEQ ID NOS:    4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial  Sequence: Designed
      primer based on the cDNA sequenc e encoding 5 alpha-reductase
      type 1

<400> SEQUENCE: 1
ccagccctgg cgatggcaac                                                   20

<210> SEQ ID NO 2
<211> LENGTH: 25
<212> TYPE: DNA
<213> ORGANISM: Artificial Sequence
<220> FEATURE:
<223> OTHER INFORMATION: Description of Artificial  Sequence: Designed
      primer based on the cDNA sequenc e encoding 5 alpha-reductase
      type 1

<400> SEQUENCE: 2
cagagcttga aattctgacc tgtta                                             25

<210> SEQ ID NO 3
<211> LENGTH: 22
<212> TYPE: DNA
<213> ORGANISM: Artificial Sequence
<220> FEATURE:
<223> OTHER INFORMATION: Description of Artificial  Sequence: Designed
      primer based on the cDNA sequenc e encoding 5 alpha-reductase
      type 1

<400> SEQUENCE: 3
acggcgcgat gcaggttcag tg                                                22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial  Sequence: Designed
      primer based on the cDNA sequenc e encoding 5 alpha-reductase
      type 1
```

-continued

```
<400> SEQUENCE: 4
agcattgtgg gagctctgct cct                                        23
```

METHOD FOR TREATMENT OF ALOPECIA

This application is a continuation-in-part of International Application PCT/JP98/03337 filed Jul. 27, 1998.

The present invention relates to a novel composition useful in the treatment of alopecia female hirsutism or seborrhea or in the prevention of bone metastasis caused by prostatic cancer.

BACKGROUND OF THE INVENTION

Excessive stimulation of androgenic hormones such as dihydrotestosterone (DHT) causes androgen-dependent alopecia (male pattern baldness or the like), acne vulgaris, seborrhea, female hirsutism, benign prostatic hypertrophy and prostatic cancer.

Steroidal anti-androgenic hormones (e.g. female hormone estrogen) are compounds which were found to be capable of treating these symptoms caused by excessive stimulation of androgenic hormones. However, they tend to bring about undesirable activities, for example, feminization, because they themselves have hormonal activity.

On the other hand, nonsteroidal anti-androgenic hormones have also been developed. In spite of being free from hormonal action, they compete with natural androgens for a receptor and therefore have undesirable activities such as feminization of a male fetus in the uterus or of a male, or initiation of a feedback mechanism so as to excessively stimulate the testis.

As 5α reductase acts on testosterone to form dihydrotestosterone (DHT), if the activity of 5α reductase can be inhibited, treatment of symptoms due to excessive stimulation of androgenic hormones without said side effects can be expected.

Human 5α reductase includes two isozymes. It has been elucidated that type I 5α reductase exists in the sebaceous glands of the face and skin, and that type II 5α reductase is distributed in the prostate.

It was expected that strong inhibition of type I 5α reductase existing in the hair follicle would alleviate male panem baldness. The effects of MK386, a selective inhibitor of type I 5-α-reductase, were evaluated using a monkey which was a model animal of male pattern baldness. As a result, the DHT level in the blood showed a 30 to 40% decrease, but such effectiveness of MK 386 was not recognized (J. Invest. Dermatol., 104, 658(1995)).

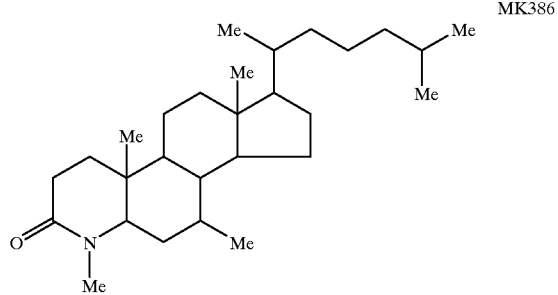

MK386

Administration of Finasteride, which is a selective inhibitor of type II 5α-reductase, to the model animal at a dose of 1 mg/kg decreased the DHT level in blood by 60 to 70%, however it was unexpectedly recognized that it was effective in the treatment of baldness (J. Clin. Endocrinol. Metabol., 79, 991(1994)).

In fact, the effects of Finasteride on human baldness have been recognized by a clinical test. The inhibition of a factor which participates in the reduction in the size of hair follicles results in such effects and it is presumed to depend on the DHT level in the blood. In addition, it has been found as a result of recent clinical tests that the strength of lowering the DHT level in the blood mainly depends on the strength of the inhibitory activity against type II 5α reductase, and that better results can be obtained by use of an inhibitor of type I 5α reductase in combination with that of type II 5α reductase (J. Clin. Endocrinol. Metabol., 81, 2942–2947 (1996)).

Also in the treatment of female hirsutism or seborrhea, a compound having inhibitory activity against type I 5α-reductase and that against type II 5α-reductase is considered to become superior, as a remedy, to a compound having only inhibitory activity against type II 5α-reductase. In order to find a more effective medicament for alopecia, female hirsutism or seborrhea, a compound which inhibits type II 5α-reductase more strongly than Finasteride and at the same time strongly inhibits type I 5α-reductase has been required.

Type II 5α-reductase is distributed in the prostate, so a compound having strong inhibitory activity against type II 5α-reductase is effective for the treatment of prostatic cancer, but it has been found recently that during the development of prostatic cancer and bone metastasis, type I 5α-reductase is in the active form [Japanese Patent Application (kokai) No. Hei 8-277220]. The compound as described above which is capable of inhibiting both of type I and type II 5α-reductases is also expected to be useful in the prevention and treatment of prostatic diseases.

The compound (I) of the present invention has been disclosed to have strong inhibitory activity against prostatic enzymes [Japanese Patent Application (kokai) Hei 5-326931. It is reasonable to expect inhibitory activity against type II 5α-reductase from the inhibitory activity against prostatic enzymes. However it is impossible to expect inhibitory activity against type I 5α-reductase, because type I 5α-reductase is not distributed in the prostate.

SUMMARY OF THE INVENTION

The present inventors carried out an extensive investigation for many years on the synthesis of derivatives having inhibitory activity against testosterone 5α-reductase and the pharmacological activity of the derivatives. As a result, it has been found that some compounds having a specific structure strongly inhibit type II 5α-reductase and moreover strongly inhibit type I 5α-reductase, and therefore they exhibit strong DHT blood level lowering activity which has not been available so far among known type II selective 5α-reductase inhibitors, and that they are useful in the treatment of alopecia, female hirsutism or seborrhea or in the prevention of the bone metastasis caused by prostatic cancer.

The present invention provides a novel composition useful in the treatment of alopecia, female hirsutism or seborrhea or in the prevention of bone metastasis caused by prostatic cancer. In another aspect, the present invention provides a use of said compound for the preparation of a composition for the treatment of alopecia, female hirsutism or seborrhea or a composition for the prevention of bone metastasis caused by prostatic cancer.

In still another aspect, the present invention provides a method for treating alopecia, female hirsutism or seborrhea or for preventing bone metastasis caused by prostatic cancer, which comprises administering a therapeutically effective amount of said compound to a warm-blooded animal in need of such treatment.

The novel composition for the treatment of alopecia of the present invention, female hirsutism or Seborrhea or for the prevention of bone metastasis caused by prostatic cancer comprises, as an active ingredient, a compound represented by formula (I) or a pharmaceutically acceptable salt thereof, preferably N-[1-methyl-1-(4-methoxyphenyl)ethyl]-3-oxo-4-aza-5α-androst-1-ene-17β-carboxamide.

The inventive method administers a compound represented by formula (I) or a pharmaceutically acceptable salt or ester or hydrate thereof for the treatment of alopecia, female hirsutism or seborrhea or the prevention of bone metastasis caused by prostatic cancer. Preferably N-[1-methyl-1-(4-methoxyphenyl)ethyl]-3-oxo-4-aza-5α-androst-1-ene-17-β-carboxamide for the preparation of said composition is used.

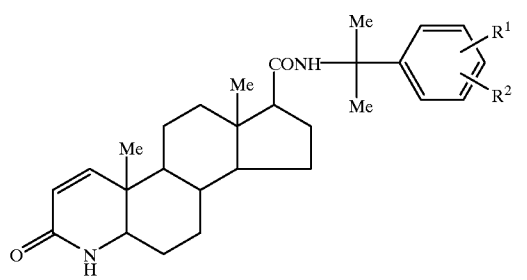

(wherein, $R^1$ and $R^2$ are the same or different from each other and each represents a hydrogen atom, a hydroxyl group, a protected hydroxyl group or a lower alkoxy group).

In the formula (I), the term "lower alkoxy group" means a straight chain or branched chain $C_{1-6}$ alkoxy group such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy, of which a straight or branched $C_{1-4}$ alkoxy group is preferred, and a methoxy group is more preferred.

The term "alopecia" means male pattern baldness and female head alopecia.

Since compound (I) can form a salt, the term "pharmaceutically acceptable salts" means the salts of the compound (I) of the present invention which can be converted to salts thereof, examples of such salts preferably include alkali metal salts such as a sodium salt, a potassium salt and a lithium salt, alkaline earth metal salts such as a calcium salt and a magnesium salt, and metal salts such as a aluminum salt, an iron salt and a zinc salt.

When the compound (I) of the present invention is allowed to stand in the atmosphere, it may absorb water thereto or to form a hydrate. Such a substance is also embraced in the present invention.

The "protecting group" of the term "protected hydroxyl group" means "conventional protecting group" or a "protecting group which can be cleaved in vivo by a biological method such as hydrolysis".

The "conventional protecting group" means a protecting group which can be cleaved by a chemical method such as hydrogenolysis, hydrolysis, electrolysis or photolysis.

Preferred examples of the "conventional protecting group" for the hydroxyl group include "lower aliphatic acyl groups" for example, lower alkylcarbonyl group such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecaroyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl, carboxyl-substituted alkylcarbonyl group such as succinoyl, glutanoyl and adipoyl, haloger-substituted alkylcarbonyl group such as chloroacetyl, dichloroacetyl, trichloroacetyl and trifluoroacetyl, lower alkoxy-substituted alkylcarbonyl group such as methoxyacethyl, unsaturated alkylcarbonyl group such as (E)-2-methyl-2-buthenoyl; "aromatic acyl groups" for example, arylcarbonyl group such as benzoyl, α-naphthoyl and β-naphthoyl, halogenated arylcarbonyl group such as 2-bromobenzoyl and 4-chloro-benzoyl, lower alkyl-substituted arylcarbonyl group such as 2,4,6-trimethylbenzoyl and 4-toluoyl, hydroxy-substituted arylcarbonyl group such as 3,5-dimethyl-4-hydroxybenzoyl and 3,5-di-t-butyl-4-hydroxybenzoyl, lower alkoxy-substituted arylcarbonyl group such as 4-anisoyl group, nitro-subatituted arylcarbonyl group such as 4-nitrobenzoyl and 2-nitro-benzoyl, lower alkoxycarbonyl-substituted arylcarbonyl group such as 2-(methoxycarbonyl)benzoyl group; aryl-substituted arylcarbonyl group such as 4-phenylbenzoyl group; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups", for example, tri(lower alkyl)silyl groups such as trimethylsilyl, triethylsilyl, isopropyldimethylsilyl, t-butyldimethylsilyl, methyldiisopropylsilyl, methyl-di-t-butylsilyl and triisopropylsilyl and tri (lower alkyl) silyl group substituted with 1 or 2 aryl groups such as diphenylmethylsilyl, diphenylbutylsilyl, diphenylisopropylsilyl and phenyldiisopropylsilyl; "alkoxymethyl groups", for example, lower alkoxymethyl groups such as methoxymethyl, 1,1-dimethyl-1-methoxymethyl, ethoxymethyl, propoxymethyl, isopropoxymethyl, butoxymethyl and tert-butoxymethyl, lower alkoxymethyl groups substituted with lower alkoxy such as 2-methoxyethoxymethyl and (halogeno lower alkoxy)methyl groups such as 2,2,2-trichloroethoxymethyl and bis(2-chloroethoxy)methyl; "substituted ethyl groups", for example, ethyl group substituted with lower alkoxy such as 1-ethoxyethyl and 1-(isopropoxy)ethyl and halogenated ethyl groups such as 2,2,2-trichloroethyl"; "aralkyl groups", for example, lower alkyl groups substituted with 1 to 3 aryl groups such as benzyl, α-naphthylmethyl, β-naphthylmethyl, diphenylmethyl, triphenylmethyl, α-naphthyldiphenylmethyl and 9-anthrylmethyl and lower alkyl groups each substituted with 1 to 3 aryl groups having an aryl substituted with a lower alkyl, halogeno (lower alkyl), lower alkoxy, nitro, halogen or cyano group such as 4-methylbenzyl, 2,4,6-trimethylbenzyl, 3,4,5-trimethylbenzyl, 3,5-di(trifluoromethyl)benzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl; "lower alkoxycarbonyl groups" such as methoxycarbonyl, ethoxycarbonyl, tert-buthoxycarbonyl and isobuthoxycarbonyl,; "lower alkenyloxycarbonyl groups" such as vinyloxycarbonyl and allyloxycarbonyl; and "aralkyloxycarbonyl groups", for example, aryl substituted with 1 or 2 lower alkoxy or nitro group such as 4-methoxylbenzyloxycarbonyl, 3,4-dimethoxylbenzyloxycarbonyl, 2-nitrobenzyloxycarbonyl and 4-nitrobenzyloxycarbonyl.

The "protecting group which can be cleaved in vivo by a biological method such as hydrolysis" means a protecting group which is cleaved in vivo by a biological method such as hydrolysis and forms a free acid or salt thereof. It can be determined whether an ester is such a derivative by administering it to an experimental animal, such as a rat or mouse, by intravenous injection, examining the body fluid of the animal after administration and detecting an original compound or a pharmaceutically acceptable salt thereof.

Preferred examples of the "protecting group which can be cleaved in vivo by a biological method such as hydrolysis" for the hydroxyl group include 1-(acyloxy) "lower alkyl groups", for example, 1-("lower aliphatic acyl" oxy) "lower alkyl groups" such as formyloxymethyl, acetoxymethyl, dimethylamincacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl, 1-("cycloalkyl" carbonyloxy) "lower alkyl groups" such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl and 1-cyclohexylcarbonyloxybutyl, and 1-("aromaticacyl" oxy) "lower alkyl groups" such as benzoyloxymethyl; (lower alkoxycarbonyloxy) alkyl groups such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy) ethyl, 1-(butoxycarbonyloxy)ethyl, 1-(isobutoxycarbonyloxy)ethyl, 1-(tert-butoxycarbonyloxy) ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy) propyl, 1-(cyclohexyloxycarbonyloxy) propyl, 1-(cyclopentyloxycarbonyioxy) butyl 1-(cyclohexyloxycarbonyloxy)butyl, 1-(cyclohexyloxycarbonyloxy)ethyl, 1-(ethoxycarbonyloxy)propyl, 2-(methoxycarbonyloxy) ethyl, 2-(ethoxycarbonyloxy)ethyl, 2-(propoxycarbonyloxy) ethyl, 2-(isopropoxycarbonyloxy)ethyl, 2-(butoxycarbonyloxy)ethyl, 2-(isobutoxycarbonyloxy) ethyl, 2-(pentyloxycarbonyloxy)ethyl, 2-(hexyloxycarbonyloxy) ethyl, 1-methoxycarbonyloxy) propyl, 1-(ethoxycarbonyloxy)propyl, 1-(propoxycarbonyloxy)propyl, 1-(isopropoxycarbonyloxy) propyl, 1-(butoxycarbonyloxy)propyl, 1-(isobutoxycarbonyloxy) propyl, 1-(pentyloxycarbonyloxy)propyl, 1-(hexyloxycarbonyloxy) propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy) butyl, 1-(isobutoxycarbonyloxy)butyl, 1-(methoxycarbonyloxy)pentyl, 1-(ethoxycarbonyloxy) pentyl, 1-(methoxycarbonyloxy)hexyl and 1-(ethoxycarbonyloxy)hexyl; and oxodioxolenylmethyl groups such as (5-phenyl-2-oxo-1,3-dioxolen-4-yl)methyl, [5-(4-methylpheyl)-2-oxo-1,3-dioxolen-4-yl]methyl, [5-(4-methoxyphenyl) -2-oxo-1,3-dioxolen-4-yl]methyl, [5-(4-fluorophenyl) -2-oxo-1,3-dioxolen-4-yl]methyl, [5-(4-chlarophenyl) -2-oxo-1,3-dioxolen-4-yl]methyl, (2-oxo-1,3-dioxolen-4-yl)methyl, (5-methyl, (5-methyl-2-oxo-1,3-dioxolen-4-yl)methyl, (5-ethyl-2-oxo-1,3-dioxolen-4-yl) methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl: "phthalidyl groups" such as phthalidyl, dimethylphthalidyl and dimethoxyphthalidyl: the above-described "lower aliphatic acyl groups" : the above-described "aromatic acyl groups": "half ester salt residue of succinic acid": "phosphate salt residue": "ester forming residues such as with amino acids": carbamoyl groups: carbamoyl group substituted with 1 or 2 lower alkyl groups: and "1-(acyloxy)alkyloxycarbonyl groups" such as pivaloyloxynethyloxycarbonyl, of which the "carbonyloxyalkyl groups" are preferred. Pharmacologically acceptable esters are preferred.

The compound (I) of the present invention may be prepared by the process shown below.

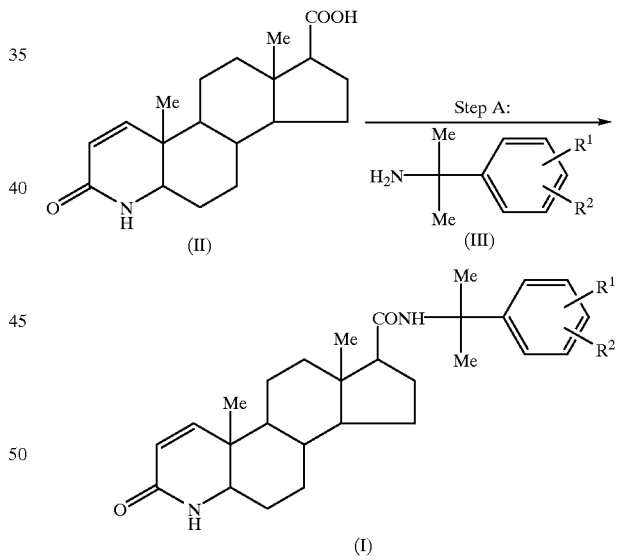

(wherein, $R^1$ and $R^2$ are as described above).

In Process A, a compound (I) is prepared by the condensation of a carboxylic acid derivative with an amine derivative.

In step A1, a compound (I) is prepared using a compound (II) or a reactive derivative thereof and a compound (III). This step is carried out in a conventional manner used in peptide synthesis, for example, an azide process, an active ester process, a mixed acid anhydride process or a condensation process.

Among these processes the azide process comprises treating an azide compound with an amine compound (III). The azide compound is prepared by the reaction of nitrous acid with a hydrazide of an amino acid, which is obtained by a reaction of compound (II) or an ester thereof with hydrazine at around room temperature in an inert solvent (e.g. dimethylformamide).

Examples of the nitrous acid compound as used herein include alkali metal nitrites such as sodium nitrite and alkyl nitrites such as isoamyl nitrite.

The reaction is effected preferably in an inert solvent and examples of the solvent as used herein include amides such as dimethylformamide and dimethylacetamide, sulfoxides such as dimethylsulfoxide and pyrrolidones such as N-methylpyrrolidone. The two step reaction of this process is carried out ordinarily in one pot. The reaction temperature ranges from −50° C. to 0° C. in the first step, while it ranges from −10° C. to 10° C. in the second step. The time required for reaction ranges from 5 minutes to 1 hour in the first step, while it ranges from 10 hours to 5 days in the second step.

The active ester process is carried out by reaction of the compound (II) with an active esterifying agent to form the active ester of the compound (II) and then by reaction of the resulting compound with the amine compound (III).

Both the reactions are carried out preferably in an inert solvent and examples of the solvent as used herein include halogenated hydrocarbons such as methylene chloride and chloroform, ethers such as ether and tetrahydrofuran, amides such as dimethylformamide and dimethylacetamide and nitriles such as acetonitrile.

Examples of the esterifying agent as used herein include N-hydroxy compounds such as N-hydroxysuccinimide, 1-hydroxybenzotriazole, N-hydroxy-5-norbornene-2,3-dicarboxyimide and disulfide compounds such as dipyridyl disulfide. The esterification is suitably effected in the presence of a condensing agent such as dicyclohexylcarbodiimide, carbonyldiimidazole or triphenylphosphine.

The reaction temperature ranges from −10° C. to 100° C. in the esterification while it is around room temperature in the reaction of the active ester compound with the amine (III). The time necessary for the reaction ranges from 30 minutes to 80 hours in each of the reactions.

In the reaction of an active ester with an amine, 4-dimethylaminopyridine or the like can be added.

The mixed acid anhydride process is carried out by reaction of a mixed acid anhydride of compound (II) with an amine.

The reaction for preparing the mixed acid anhydride is achieved by reaction of a compound (II) with an agent forming a mixed acid anhydride. Examples of such an agent include a lower ($C_1$–$C_4$) alkyl halogenated carbonate such as ethyl chlorocarbonate or isobutyl chlorocarbonate, a lower alkanoyl halide such as pivaloyl chloride, a (lower alkyl)- or diaryl-cyanophosphoric acid such as diethyl cyanophosphoric acid or diphenyl cyanophosphoric acid, or a sulfonyl halide such as 2,4.6-triisopropylbenzenesulfonyl chloride, paratoluenesulfonyl chloride or methanesulfonyl chloride.

The reaction is carried out suitably in the presence of an organic amine such as trimethylamine or N-methylmorpholine at −10° C. to 50° C. The time necessary for the reaction ranges from 30 minutes to 20 hours.

The reaction of a mixed acid anhydride and an amine (III) is conducted suitably in an inert solvent (for example, the above-exemplified halogenated hydrocarbon, amide or ether) in the presence of the above-exemplified organic amine. The reaction temperature ranges from 0° C. to 80° C. and the time necessary for the reaction ranges from 1 hour to 48 hours.

Alternatively, process A is carried out in the mixture of a compound (II), a compound (III) and an agent forming the corresponding mixed acid anhydride without isolation of the mixed acid anhydride.

The condensation process is carried out by directly reacting the compound (II) with the amine (III) in the presence of a condensing agent such as dicyclohexylcarbodiimide, carbonyl diimidazole, 1-methyl-2-chloro-pyridinium iodide-triethylamine. This reaction is carried out under conditions similar to those employed in the above-described reaction for the preparation of an active ester.

When $R^1$ or $R^2$ contains a protected hydroxyl group, the protecting group can be removed in a conventional manner.

Starting compound (II) or active ester thereof is a known compound or prepared by a procedure familiar to those skilled in the art [for example, J. Med. Chem., 27, 1690 (1984); J. Med. Chem., 29, 2298(1986)].

Compound (III) is a known compound or prepared by one skilled in the art (for example,
Synthesis, 593(1976);
J. Org. Chem., 36, 305(1971);
Angew. Chem., 82, 138(1970);
Synthesis, 24(1978);
Synthetic Commun., 18, 777(1988);
Synthetic Commun., 18, 783(1988);
Organic Reaction, 3, 337(1946);
Org. Synthesis, 51, 48(1971);
Tetrahedron, 30, 2151(1974);
J. Org. Chem. 37, 188(1972)]. For example, $H_2N$—$C(Me)(Me)$—$Ph(R^1)(R^2)$ which is a starting compound of the present invention can be prepared as shown in the following reaction scheme:

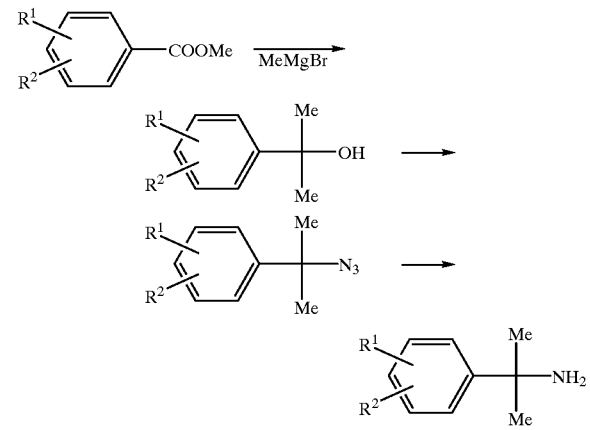

(wherein,
$R^1$ and $R^2$ are as described above.
Me represents a methyl group and Ph represents a phenyl group) by Grignard reaction, substitution reaction of a hydroxyl group with azide group and then reduction of azide group in a similar process to that described in Synthesis. 24(1978).

Compound (I) is administered orally in the form of tablets, capsules, granules, powders, syrups or the like and locally in the form of an ethanol solution, cleansing foam, cleansing cream, skin gel, skin lotion, shampoo gel, cream shampoo or the like.

Oral pharmaceutical formulations are prepared by procedures familiar to those skilled in the art by using excipients (examples include organic excipients, e.g., sugar derivatives such as lactose, sucrose, glucose, mannitol and sorbitol;

starch derivatives such as corn starch, potato starch, α-starch, dextrin and carboxymethyl starch; cellulose derivatives such as crystalline cellulose, low-substituted hydroxypropyl cellulose, hydroxypropylmethyl cellulose, carboxymethyl cellulose, calcium carboxymethyl cellulose and sodium internally cross-linked carboxymethyl cellulose; gum arabic; dextran; and pullulan; and inorganic excipients. e.g., silicate derivatives such as light silicic acid anhydride, synthetic aluminum silicate and magnesium aluminate metasilicate, phosphates such as calcium phosphate; carbonates such as calcium carbonate and sulfates such as calcium sulfate), lubricants (examples include stearic acid, metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; sodium salts of aliphatic acid; lauryl sulfates such as sodium lauryl sulfate and magnesium lauryl sulfate; silicic acids such as silicic acid anhydride and silicic hydrate; and the above-exemplified starch derivatives), binders (examples include polyvinyl pyrrolidone, Macrogol and compounds similar to the above-exemplified excipients), disintegrants (examples include compounds similar to the above-exemplified excipients and chemically-modified starches and celluloses such as sodium cross carmellose, sodium carboxymethyl starch and crosslinked polyvinylpyrrolidone), stabilizers (examples include paraoxybenzoates such as methyl paraben; and propyl paraben, alcohols such as chlorobutanol, benzyl alcohol and phenylethyl alcohol; benzalkonium chloride; phenol derivatives such as phenol and cresol; thimerosal; dehydroacetic acid, and sorbic acid), corrigents (examples include ordinarily-employed sweeteners, acidifiers and flavors) and/or diluents.

Local pharmaceutical formulations are prepared by adding an exemplified compound to a base well known to those skilled in the art; for example, suspending agents (examples include gum arabic, tragacanth, methyl cellulose, sodium carboxymethylcellulose, hydroxyethyl cellulose, hydroxypropyl cellulose, sodium alginate and bentonite), emulsifying agents (examples include triethanolamine, sodium lauryl sulfate, sorbitan sesquioleate, polysorbate 80 and stearic acid polyoxyl 40), moistening agents (examples include sorbitol, ethylene glycol, propylene glycol, butylene glycol and glycerin), preservatives (examples include methyl paraoxybenzoate, ethyl paraoxybenzoate, propyl paraoxybenzoate and butyl paraoxybenzoate) or solvents (examples include water; alcohols such as ethanol, isopropyl alcohol, propylene glycol, cetanol and isostearyl alcohol; hydrocarbons such as natural fats and oils, waxes and liquid paraffin; aliphatic acids such as stearic acid, isostearic acid, oleic acid and linoleic acid; and esters such as isopropyl myristate) or a mixture thereof.

The amount of the compound (I) to be orally administered or locally administered will vary depending on the condition, age or the like of the patient and the specific condition (i.e., alopecia, female hirsutism or seborrhea) which is being treated or the condition which is being prevented (the specified bone metastasis). It is desirably administered in one dose of 0.001 mg/kg weight (preferably 0.01 mg/kg weight) as a lower limit and 10 mg/kg weight (preferably 0.5 mg/kg weight) as an upper limit and administered in a single dose or in several divided doses a day.

THE EXAMPLES

The present invention will hereinafter be described more specifically by test, referential examples and Preparation Examples.

Test Example 1

Method for Determination of the Inhibitory Activity Against Each of Type I and Type II Human 5α-reductases (1) Preparation of recombinant human type I and type II 5α-reductases a) Cloning 2 cDNAs of recombinant human type I and type II 5α-reductases In order to clone the entirely translated regions of type I and type II human 5α-reductases by a polymerase chain reaction (PCR) method, primers of Sequence ID. Nos. 1,2,3 and 4 were prepared using an Oligo 1000 DNA synthesizer (product of BECKMAN Co., Ltd.) on the basis of the base sequences of type I and type II human 5α-reductases described in published reports (Stefan. A, et al., Proc. Natl. Acad. Sci. USA, 87, 3640–3644(1990). Stefan. A, et al. Nature, 354. 159–161(1991)).

Type I Sense.primer: 5'-CCAGCCCTGGCGATGGCAAC-3' (Sequence ID No. 1)

Type I Antisense.primer: 5'-CAGAGCTTGAAATTCTGACCTGTTA-3' (Sequence ID. No. 2)

Type II Sense.primer: 5'-ACGGCGCGATGCAGGTTCAGTG-3' (Sequence ID. No. 3)

Type II Antisense.primer: 5'-AGCATTGTGGGAGCTCTGCTCCT-3' (Sequence ID. No. 4)

As a template for the PCR method. Human Liver QUICK-Clone™ cDNA and Human Prostate QUICK-Clone™ cDNA (products of CLONTECH Laboratories, Inc.) were employed.

PCR was carried out using 1 μl of cDNA. 5 μl of a PCR buffer attached. 1 μl of a 10 mM dNTP mixed solution. 1 μl each of the above-described sense and antisense-primers at a concentration of 20 μl M. 1 μl of 5 unit/ml of TaKaRa Taq polymerase and 40 μl of distilled water to give a reaction volume of 50 μl. For PCR, a cycle of the reactions at 94° C. for 20 seconds, at 55° C. for 1 minute and at 72° C. for 1 minute was repeated 25 times, followed by storing at 4° C. When a portion of about 5 μl of the PCR reaction mixture was subjected to 0.8% agarose gel electrochromatography, two bands (type I: 1021 bp. type II: 812 bp) corresponding to those expected from the above-described literature were found. The remaining portion of the PCR reaction mixture was therefore purified by 5% acrylamide gel electrochromatography. The cDNA fragment thus purified was subcloned using a TA Cloning™ Kit (product of Invitrogen Corporation). It was confirmed as a result of the analysis of the entire base sequence of each of the subcloned type I and type II cDNAs by the dye terminator method that they had the same sequences as those of the described reports. The type I and type II cDNAs whose base sequences had thus been confirmed were inserted in an expression vector, allowed to express and then provided for use.

b) Preparation of Type I and Type II Human Expression Plasmids

The *Escherichia coli* strain DHS (supE44, hsdR17, recA1, endA1, gyrA96, thi-1, re1A1) (purchased from: Toyobo Co., Ltd.) was transformed using pME18sH5R1 or pME18sH5R2, that is, the type I or type II human expression plasmid, by the method described in the document attached to TA Cloning™ Kit. About 10 μl of the primary culture solution of the recombinant strain was implanted in 50 ml of a 2×LB medium (20 g of Bacto-Tryptone (product of DIFCO Labs.), 10 g of Bacto-Yeast Extract (product of DIFCO Labs.), 10 g of sodium chloride and 2 g of glucose/l L) containing 50 μg/ml of ampicillin (product of GIBCO BRL), followed by incubation at 37° C. for about 40 hours. The culture solution was subjected to centrifuation (5000 rpm, 10 minutes) and the cells were collected. From the resulting cells, pME18sH5R1 or pME18sH5R2 was prepared using a QIAGEN Plasmid Maxi Kit (product of Qiagen Inc.).

c) Expression and Preparation of Type I and Type II Human Proteins

To $2 \times 10^6/0.5$ ml of COS-1 cells, 10 to 20 μg of pME18sH5R1 or pME18sH5R2 was introduced by the electroporation method (Gene Pulser™; product of Bio-Rad Laboratories), 960 μF. 200Ω, 300 V). After the introduction the mixture was incubated for about 48 hours and cells were collected. The cells were homogenized (1000 rpm, 30 seconds) by POLYTRON (product of KINEMATICA GmbH) in a buffer solution (20 mM potassium phosphate buffer solution, pH 7.4, 10% glycerol, 0.33M sucros, 50 μM nicotinamide adenine dinucleotide phosphate reduced form (NADPH), and 0.001% phenylmethylsulfonyl fluoride (PMSF)) in an ice bath, followed by centrifugation ($10000 \times$ g. 1 hour). The precipitate was suspended again in the buffer solution and the resulting suspension was stored at $-80°$ C. The suspension was used as type I or type II human 5α-reductase.

(2) Measurement of Protein Content

The protein content was measured by the Bradford method (Bio-Rad Protein Assay of Biorad) by using bovine gamma-globulin (bovine cohn fraction II, product of Sigma) as a standard product.

(3) Determination of 5α-reductase Activity

The 5α-reductase activity was determined using the ratio of conversion of $^{14}C$ testosterone (product of Amersham) to $^{14}C$ 5α-dihydrotestosterone as an index. A compound was dissolved in and diluted with dimethylsulfoxide (DMSO). To each of two test tubes, a 5 μl-portion of the resulting solution was poured, while 5 μl of only DMSO was poured to a further test tube as a control group. To each of the test tubes was added 0.5 ml of an enzyme reaction buffer solution containing 10 to 25 μg of the recombinant type I or type II human 5α-reductase (type I; a 40 mM calcium phosphate buffer solution (pH 7.5) containing 1 μM $^{14}C$ testosterone, 1 mM dithiothreitol and 0.5 mM NADPH, type II; a 100 mM tris-citrate buffer solution (pH 5.5) containing 1 μM $^{14}C$ testosterone, 1 mM dithiothreitol and 1 mM NADPH), followed by incubation at 37° C. for 15 minutes. After the incubation, 2 ml of ethyl acetate (containing testosterone, 5α-dihydrotestosterone and androstenedione, each 10 μg) was added and the resulting mixture was stirred sufficiently, whereby the enzymatic reaction was terminated and the steroidal compounds were extracted in the ethyl acetate layer. The ethyl acetate phase was then separated from the aqueous phase by centrifugation (3000 rpm for 5 minutes). The ethyl acetate phase was transferred to another test tube, followed by evaporation to dryness under a stream of nitrogen gas. The wall of the test tube was washed with 0.8 ml of diethyl ether, whereby the steroidal compounds were washed away to the bottom of the test tube. After evaporation to dryness again, the steroidal compound was dissolved in 40 μl of ethyl acetate and the resulting solution was spotted on a thin layer plate (LK6DF silica plate, product of Whatman). The thin layer plate was developed with a 1:1 mixture of ethyl acetate and cyclohexane twice, to separate each fraction containing a steroidal compound. The radioactivity of each fraction was determined by a bioimage analyzer (product of Fuji Film Co., Ltd.). The inhibitory activity against the reductase was indicated by 50% inhibitory concentration ($IC_{50}$).

The $IC_{50}$ value was calculated as follows: Taking the conversion ratio of the control group as 100% the inhibition ratio of the activity of the reductase (100−(conversion ratio upon addition of test compound÷conversion ratio of control group)×100) (%) was calculated. A dilution row of the compound was made and the inhibition ratio at each concentration was calculated by the above-described method. By using the dilution concentration at which the inhibition ratio falls within a range of about 20% to about 80% and setting the log value of the concentration of the test compound as X and the inhibition ratio as Y, the regression line was calculated by the method of least squares. From the resulting regression line, the concentration of the compound required to give a 50% inhibition ratio was calculated and it was designated as $IC_{50}$.

The $IC_{50}$ of the type I is shown in Table 1, while that of the type II is shown in Table 2.

TABLE 1

(Type I)

| Compound | $IC_{50}$ |
|---|---|
| Compound of Reference Example 1 | $4.9 \times 10^{-8}$ M |
| Finasteride | $7.0 \times 10^{-7}$ M |

TABLE 2

(Type II)

| Compound | $IC_{50}$ |
|---|---|
| Compound of Reference Example 1 | $3.2 \times 10^{-9}$ M |
| Finasteride | $1.5 \times 10^{-8}$ M |

Test Example 2

Effects for Lowering the Dihydrosterone Level in Human Blood

To a human body, 1 to 10 mg/body of Compound I or 5 mg/body of Finasteride was orally administered and the dihydrotestosterone (DHT) and testosterone (T) levels in blood were measured. Their ratios (DHT/T) before administration (pre) and after passage of time (10 and 18 hours) were calculated, from which (DHT/T)/(DHT/T)pre was calculated. The results are shown in Table 3 (n=4 to 6).

TABLE 3

| | After 10 hours | After 18 hours |
|---|---|---|
| Compound of Reference Example 1 | | |
| (1 mg) | 0.518 | 0.525 |
| (5 mg) | 0.411 | 0.376 |
| (10 mg) | 0.279 | 0.284 |
| Finasteride | | |
| (5 mg) | 0.553 | 0.461 |

Test Example 3

Test Using Human Papilla Pili Cells

Papilla pili is a cell mass which exists in a small number in hair follicles. At present, it is presumed to be a stem cell for forming the base for hair growth. This cell is found to have 5α-reductase activity. It is therefore possible to carry out a test of a 5α-reductase inhibitor by using a cultivated system of this cell. Isolation and incubation of papilla pili cells is carried out by the method of Messenger. A. G. (The Culture of Dermal Papilla Cells From Human Hair Follicles, Br. J. Dermatol., 110, 685–989(1984)) or Itami, S. et al., ("5α-Reductase Activity In Cultured human Dermal Papilla Cells From Beard Compared With Reticular Dermal Fibroblasts", J. Invest. Dermatol., 94, 150–152(1990)). Beard papilla cells and hair roots at the occipital region of the heads of two subjects are provided for the test. The tests are all carried out under confluent conditions after these cells are subcultured over 4 to 6 generations. The cells which have become confluent are washed twice with a phosphate-buffered saline (PBS), peeled by a rubber policeman and then collected in a centrifugal tube. The cells are subjected to centrifugation at 4° C. under 1500 rpm for 10 minutes. The resulting pellet is suspended in a buffer solution (a 20 mM tris-hydrogen chloride buffer solution (pH 7.5) containing 250 mM sucrose, 1 mM magnesium chloride and 2 mM calcium chloride) and a needle of 25 G is allowed to pass through it 10 times. The suspension is then homogenized using a Teflon-glass homogenizer to obtain a solution of disrupted cells. In order to identify the localization of 5α-reductase in the cell, the resulting solution of disrupted cells is subjected to centrifugation under 800×g for 10 minutes, whereby a crude nucleus fraction is obtained. The supernatant is centrifuged under 10,000 g for 15 minutes, whereby a mitochondrion fraction is obtained. The supernatant is centrifuged further under 100,000×g for 60 minutes, whereby a microsome fraction and a cytosol fraction are obtained. The precipitated porion of each of them is washed twice, followed by re-suspension.

Under conventional incubation conditions, 50 µl of the solution of disrupted cells is added to 100 mM sodium citrate (pH 5.5) or 100 mM tris-hydrogen chloride (pH 7.5) containing 50 nM [$^3$H]-testosterone and 1 mM NADPH to give a 100 µl solution. To each tube, the solution of disrupted cells is added in an amount of 50 to 100 mg in terms of a protein content. The reaction is carried out at 37° C. for 30 minutes. During the incubation, the reaction proceeds in proportion to time. In order to find the optimum pH for the reaction, a citrate buffer solution is used at pH 4.5 to 6.5, while a tris-hydrogen chloride buffer solution is used at pH 7.0 to 9.0. The protein content is measured by the method of Lowvry. et al. ("Protein Measurement With The Folin Phenol Reagent", J. Biol. Chem. 193, 265–275(1951)).

After completion of the incubation, the reaction is terminated by the addition of 4 times the amount of chloroform-methanol (2/1: V/V) containing 110 mg of each carrier steroid. The extracted steroid is analyzed by thin-layer chromatography in accordance with the method of Gomez et al. ("In Vitro Metabolism Of Testosterone-4-$^{14}$C and D-androstene-3,17-dione-4-$^{14}$C In Human Skin", Biochem., 7, 24–32(1968)). The purity of each steroid is confirmed by the recrystallization method. The 5α-reductase activity is indicated by the amount of dihydrotestosterone formed. The enzyme inhibitory action is indicated as percent inhibition (100−(conversion ratio upon addition of test compound÷conversion ratio of control group)×100) (%), setting the conversion ratio of the control group at 100%.

The compounds of formula (I) are found to exhibit superior 5α-reductase inhibitory activity Test Example 4

Prevention of Epilation and Trichogenous Effect in Stumptailed Macague (1)

The stumptailed Macaque suffers from alopecia which resembles male pattern alopecia. The alopecia of stumptailed Macaque starts just after puberty (about 4 years old). Alopecia attacks almost all of both male and female stumptailed Macaques and it depends on androgen levels. The stumptailed Macaque is therefore a useful animal model of human male pattern alopecia.

Male stumptailed Macaques (3 to 16 years old) are classified into groups, each consisting of 3 to 6 animals. The scalp of the stumptailed Macaque is clearly divided into frontal region and occipital region and one of these regions is marked, for example, with Chinese ink. The hair on the marked region is shaven off. A solution or powder of a test compound is prepared at various doses and in various combinations and these samples are uniformly applied to the region from which the hair has been shaven off, or it is orally administered. To a control animal, the same amount of a solvent (e.g. dimethylsulfoxide), cream (subcutaneous administration) or placebo (oral administration) is administered. The hair of the marked region is shaven off at intervals of 4 to 6 weeks and the amount of the hair shaven off is weighed. The administration is continued for 6 weeks to 2 years. Finasteride is a 5α-reductase inhibitor and is known to prevent the alopecia of the above-described animal. Finasteride (oral administration) is provided for the test as a comparison.

The scalp (4 mm of punch), as a biopsy specimen, is resected at the start and end of the test. The presence or absence of alopecia is judged by the analysis of the 5-αreductase activity and tissue inspection of the resected scalp.

The compounds of formula (I) are found to be effective for alopecia.

Test Example 5

Prevention of Epilation and Trichogenous Effect in Stumptailed Macague (2)

Male and female stumptailed Macaques (3 to 16 years old) are divided into groups, each consisting of 3 to 6 animals. A solution or powder of a test compound is prepared at various doses and in various combinations and uniformly applied to the scalp at the frontal region, or it is orally administered once a day. Administration is continued for 6 weeks to 2 years. To a control animal, the same amount of a solvent (e.g. dimethylsulfoxide), cream (subcutaneous administration) or placebo (oral administration) is administered. The hair condition at the frontal region is observed at intervals of 1 month and effects of the test compound are evaluated from the size of the hair diameter, density, and trichogenous region and time. At the same time, a picture of the stumptailed Macaques is taken and the effect on the whole is judged from the pictures. A portion of the skin (a circle of 4 mm in diameter) at the frontal region of the head is resected as a biopsy specimen at the start of the test and Month 3 and Month 6 after the start and effects on the growth stages of the hair root are studied by a histological analysis.

The compounds of formula (I) are found to be effective for alopecia.

Test Example 6

Test Using Fuzzy Rat

A fuzzy rat is an androgen-dependent model animal which shows abnormal sthenia of proliferation of and secretion from sebaceous gland cells at the hair root. Its hair roots in the juvenile stage (about 4 weeks old) are mainly of that in the growth stage. After the sexual maturation (around 8 weeks), the hair roots at the resting stage increase. It is therefore used as a model animal for investigating influence on hair growth.

Fuzzy rats (male, 2 to 12 weeks old) are divided into groups, each group consisting of 5 to 6 rats. A solution or powder of a test compound is prepared at various doses and in various combinations and uniformly applied to the skin at the dorsal region, or it is orally administered once a day. Administration is continued for 4 to 8 weeks. To animals of the control group, the same amount of a solvent (e.g. dimethylsulfoxide), cream (subcutaneous administration) or placebo (oral administration) is administered. On the next day after completion of the administration, they were decapitated. The skin tissue (circle of 4 mm in diameter) at the dorsal region was resected. Effects on the sebaceous gland and hair growth stage at the hair root are studied by a histological analysis.

The compounds of formula (I) are found to be effective for seborrhea and alopecia.

As well as the above-described tests, hair growth can be evaluated in accordance with the method described in a literature (B de Brouwer et al. Br. J. Dermatol., 137, 699–702(1997)) by using a nude mouse.

Reference Example 1

N-[1-Methyl1-(4-methoxyphenyl)ethyl]-3-oxo4-aza-5α-androsto-1-ene-17β-carboxamide To 30 ml of dried toluene, 1.0 g of 3-oxo-4-aza-5α-androst-1-ene-17β-carboxylic acid, 1.6 g of triphenylphosphine and 1.4 g of 2.2'-dipyridyl disulfide were successively added. The resulting mixture was stirred overnight at room temperature. The reaction mixture was subjected to column chromatography on 35 g of silica gel eluting with acetone-methylene chloride (1:9 to 1:1), to afford 1.11 g of the 2-pyridylthioester compound. To 30 ml of dried methylene chloride, 5.0 g of the 2-pyridylthioester compound and 5.0 g of 1-(4-methoxyphenyl)-1-methylethylamine were successively added and the resulting mixture was stirred at room temperature for 3 days. After dilution with 100 ml of methylene chloride, the mixture was washed successively with 1N-hydrochloric acid, water, an aqueous solution of sodium bicarbonate and saturated saline, dried over anhydrous magnesium sulfate and concentrated under reduced pressure. The residue was subjected to column chromatography on 15 g of silica gel eluting with acetone—methylene chloride (1:9 to 1:1), to give 5.2 g of the title compound.

NMR spectrum (CDCl$_3$) δ ppm: 0.68(3H,s), 0.98(3H,s), 0.90–2.20(16H,m). 1.70(3H,s), 1.72(3H,s), 3.35(1H,t,J=9Hz), 3.80(3H,s), 5.48(1H,br.), 5.76(1H,br.), 5.83(1H,d,J=10 Hz), 6.82(1H,d,J=10 Hz), 6.88(2H,d,J=9 Hz), 7.32(2H,d,J=9 Hz).

IR spectrum $v_{max}$ cm$^{-1}$(KBr): 2969, 2938, 1672, 1599, 1514, 1455, 1248, 1181, 1035, 825.

Preparation Example 1
Tablets
(5-mg tablet)

| Component | Basic formulation (mg/tablet) |
|---|---|
| Compound of Reference Example 1 | 5 |
| Hydroxypropylmethyl cellulose | 15 |
| Sodium carboxymethyl starch | 9.5 |
| Crystalline cellulose | 30.5 |

-continued

| | | |
|---|---|---|
| Sodium cross carmelose | 20 | |
| Lactose (after sieving) | 38.75 | |
| Yellow iron sesquioxide | 0.05 | |
| Magnesium stearate (after sieving) | 1.2 | |
| Tablets | 120.0 | |

Preparation Example 2
Alcohol solution

| | | |
|---|---|---|
| Compound of Reference Example 1 | 15.0 | (wt. %) |
| Water | 45 | |
| Ethanol | 40 | |

Preparation Example 3
Cleansing Foam

| | | |
|---|---|---|
| Compound of Reference Example 1 | 10.00 | (wt. %) |
| Water | 70.439 | |
| Chamomile | 0.01 | |
| Aloe vera gel | 0.01 | |
| Allantoin | 0.001 | |
| Triethanolamine | 0.02 | |
| METHOCEL (METHOCEL ™ 40-100 (Dow)) | 1.50 | |
| Glycerin | 3.00 | |
| Sodium lauryl sulfate | 15.00 | |
| Vitamin A oil | 0.01 | |
| Vitamin E oil | 0.01 | |

Preparation Example 4
Cleansing cream

| | | |
|---|---|---|
| Compound of Reference Example 1 | 5.0 | (wt. %) |
| Synthetic beeswax | 14.0 | |
| PPG$_2$ myristyl propionate | 5.0 | |
| Lanolin alcohol | 0.5 | |
| Mineral oil | 36.0 | |
| Propyl paraben | 0.15 | |
| Borax | 1.0 | |
| Water | 38.35 | |

Preparation Example 5
Skin gel

| | | |
|---|---|---|
| Compound of Reference Example 1 | 2.00 | (wt. %) |
| PPG$_2$ myristyl ether propionate | 45.0 | |
| PPG$_{10}$ cetyl ether | 5.0 | |
| C$_{18}$–C$_{36}$ triglyceride | 4.0 | |
| Myristyl myristate | 3.0 | |
| Glyceryl tribehenate | 2.0 | |
| Cyclomethicone | 34.00 | |
| Polyethylene | 5.00 | |

Preparation Example 6
Skin lotion

| | | |
|---|---|---|
| Compound of Reference Example 1 | 1.0 | (wt. %) |
| Diethanol amine oleth-3 phosphate | 1.0 | |
| Emulsified wax | 2.0 | |
| C$_{18}$–C$_{36}$ wax aliphatic acid | 1.0 | |
| PPG$_2$ myristyl propionate | 5.0 | |
| Glycerin | 3.0 | |
| Triethanolamine | 0.5 | |
| Water | 86.5 | |

Preparation Example 7
Shampoo gel

| | | |
|---|---|---|
| Compound of Reference Example 1 | 2.0 | (wt. %) |
| Isopropanolamine lauryl sulfate | 81.5 | |
| Coconut oil aliphatic acid diethanol amide | 8.0 | |
| C$_{18}$–C$_{36}$ wax acid glyceryl ester | 4.5 | |
| PPG$_5$ ceteth-10 phosphate | 4.0 | |

Preparation Example 8
Cream shampoo

| | | |
|---|---|---|
| Compound of Reference Example 1 | 0.1 | (wt. %) |
| Sodium lauryl sulfate | 65.0 | |
| Glyceryl tribebenate | 2.0 | |
| Hydrolyzed collagen | 1.0 | |
| Lauric acid diethanolamide | 5.0 | |
| Water | 26.9 | |

PPG: polyethylene glycol polypropylene glycol

Finasteride is a compound which is marketed in the United States as a medicament for benign prostatic hypertrophy and as a medicament for alopecia.

The compound (I) of the present invention and compounds related thereto have stronger inhibitory action against type II isozyme than that of Finasteride. They also have strong inhibitory action against type I isozyme. They have such a stronger DHT lowering action in the blood than Finasteride and have such a low toxicity that they are useful as an active ingredient of a composition for the treatment of alopecia, female hirsutism or seborrhea, or of a composition for the prevention of bone metastasis caused by prostatic cancer.

Free text of Sequence List
Sequence Listing ID. No. 1
　　Description of synthesized sequence: a primer designed on the basis of cDNA sequence encoding type I 5α-reductase.
Sequence Listing ID No. 2
　　Description of synthesized sequence: a primer designed on the basis of cDNA sequence encoding type I 5α-reductase.
Sequence Listing ID No. 3
　　Description of synthesized sequence: a primer designed on the basis of cDNA sequence encoding type II 5α-reductase.
Sequence Listing ID No. 4
　　Description of synthesized sequence: a primer designed on the basis of cDNA sequence encoding type II 5α-reductase.

We claim:

1. A method for the treatment of alopecia which comprises administering to a warm-blooded animal in need thereof a therapeutically effective amount of a compound comprising N-[1-methyl-1-(4-methoxyphenyl)ethyl]-3-oxo-4-aza-5α-androst-1-ene-17β-carbaxamide or a pharmaceutically acceptable salt or ester or hydrate thereof.

2. The method according to claim 1, wherein the warm-blooded animal is a human.

3. The method according to claim 2, wherein the compound is administered in a dose of 0.001 to 10 mg/kg.

4. The method according to claim 2, wherein the compound is administered in a dose of 0.1 to 0.5 mg/kg.

5. The method according to claim 2, wherein the compound is administered orally.

6. The method according to claim 2, wherein the compound is administered locally.

* * * * *

UNITED STATES PATENT AND TRADEMARK OFFICE
CERTIFICATE OF CORRECTION

PATENT NO. : 6,380,179 B1  Page 1 of 1
DATED : April 30, 2002
INVENTOR(S) : Koichi Kojima et al.

It is certified that error appears in the above-identified patent and that said Letters Patent is hereby corrected as shown below:

Column 16,
Line 66, delete "PPG: polyethylene glycol polypropylene glycol".

Signed and Sealed this

Second Day of December, 2003

JAMES E. ROGAN
*Director of the United States Patent and Trademark Office*